US005893363A

United States Patent [19]
Little et al.

[11] Patent Number: 5,893,363
[45] Date of Patent: Apr. 13, 1999

[54] ULTRASONIC ARRAY TRANSDUCER TRANSCEIVER FOR A HAND HELD ULTRASONIC DIAGNOSTIC INSTRUMENT

[75] Inventors: Blake W. Little, Bothell; Lauren S. Plflugrath, Seattle; Juin-Jet Hwang, Mercer Island, all of Wash.

[73] Assignee: SonoSight, Inc., Bothell, Wash.

[21] Appl. No.: 08/826,543

[22] Filed: Apr. 3, 1997

Related U.S. Application Data

[63] Continuation-in-part of application No. 08/672,782, Jun. 28, 1996, Pat. No. 5,722,412.

[51] Int. Cl.$^6$ ........................................... A61B 8/00
[52] U.S. Cl. ........................................... 600/447
[58] Field of Search ..................... 600/444, 445, 600/446, 447, 459

[56] References Cited

U.S. PATENT DOCUMENTS

| | | | |
|---|---|---|---|
| 5,295,485 | 3/1994 | Shinomura et al. | 128/660.07 |
| 5,360,005 | 11/1994 | Wilk | 128/653.1 |
| 5,520,187 | 5/1996 | Snyder | 600/459 |
| 5,590,658 | 1/1997 | Chiang et al. | 128/661.01 |
| 5,690,114 | 11/1997 | Chiang et al. | |

OTHER PUBLICATIONS

Minivisor Service Manual from Organon Teknika (Sep. 1979).
Ultra PCI System Specifications from Advanced Medical Products of Columbia, South Carolina (date unknown).
"Micros Q.V." brochure by Advanced Medical Products, Inc. (Sep. 1996).

Primary Examiner—George Manuel
Attorney, Agent, or Firm—W. Brinton Yorks, Jr.

[57] ABSTRACT

A hand held ultrasonic instrument is provided in a portable unit which performs both B mode and Doppler imaging. The instrument includes a transducer array mounted in a hand-held enclosure, with an integrated circuit transceiver connected to the elements of the array just behind the transducer. The transceiver is controlled by, and provides received echo signals to, a digital beamformer mounted in the hand-held enclosure.

48 Claims, 9 Drawing Sheets

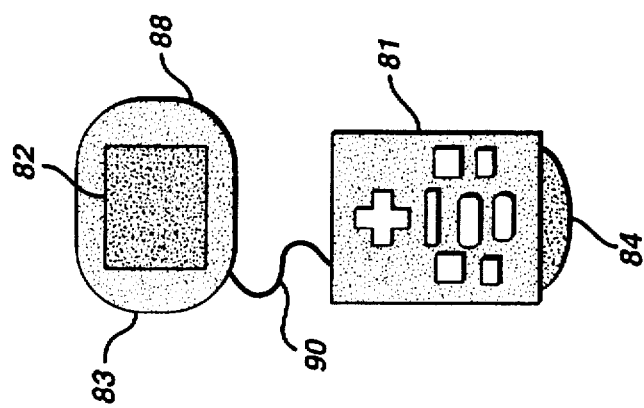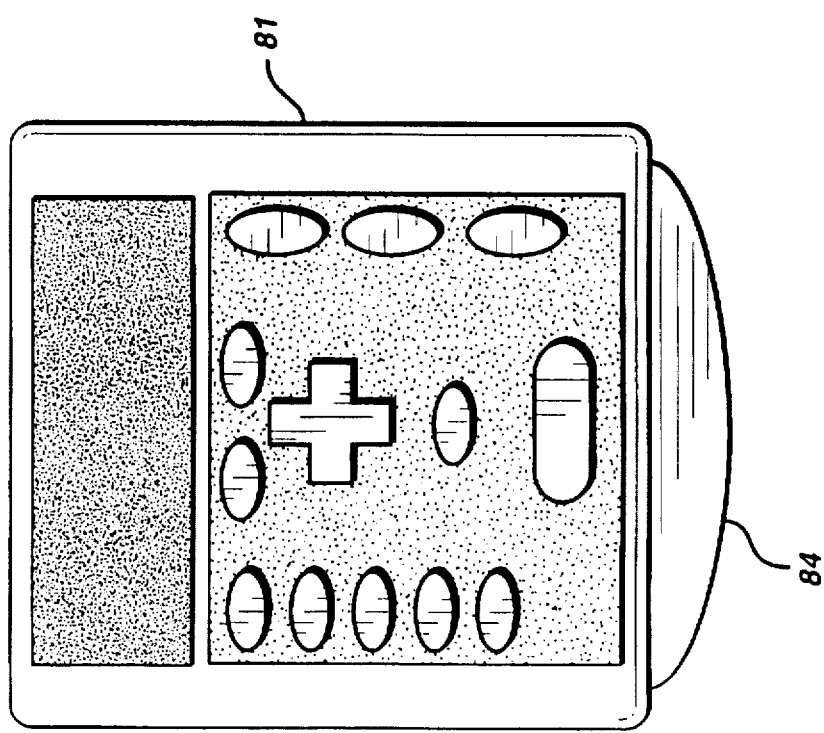

FIG. 10

| SWITCH FUNCTION | | DESCRIPTION | NUMBER OF CONTACTS |
|---|---|---|---|
| POWER OFF/ON | ⊂⊃ | SLIDE SWITCH | 1 |
| ACTIVE SCAN/FREEZE | ⬭ | PUSH AND HOLD FOR ACTIVE SCAN | 1 |
| CPA | ○ | ENABLES AND DISABLES COLOR POWER ANGIO CPA | 1 |
| DOPPLER/CPA FILTER | ○ | HIGH/MEDIUM/LOW BUTTON CYCLES THROUGH 3 SELECTIONS | 1 |
| 3D IMAGING MODE | ○ | ENABLES 3D CAPTURE WHEN ENGAGED BEFORE THE ACTIVE SCAN BUTTON IS PUSHED | 1 |
| PRINT | ○ | SENDS SERIAL SIGNAL TO PRINTER | 1 |
| CURSOR POSITION | ✛ | X/Y POSITION OF CURSOR | 4 |
| ENTER | ○ | ENTERS SELECTION | 1 |
| MENU | ○ | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID, PATIENT NAME, CINE 2D AND 3D REVIEW | 1 |
| MEASURE | ○ | ENABLES MEASUREMENTS, USES CURSOR AND ENTER | 1 |
| FOCUS | ○ | ENABLES FOCUS MODE, CURSOR UP DOWN POSITIONS FOCUS, CURSOR LEFT RIGHT SELECTS NUMBER OF ZONES | 1 |
| IMAGE | ⊚⊚ | ALLOWS THE USER TO SELECT THROUGH SEVERAL GRAY SCALE CURVES, SPATIAL AND TEMPORAL FILTERS WITH IN A PREDETERMINED SET OF SETUPS FOR A SELECTED APPLICATION | 2 |
| DEPTH | ⊚⊚ | UP/DOWN, 5 DEPTH SELECTIONS | 2 |
| TGC GAIN | ⊚⊚ | UP/DOWN | 2 |
| BRIGHTNESS | ⊚⊚ | LCD DISPLAY CONTROL UP/DOWN | 2 |
| CONTRAST | ⊚⊚ | LCD DISPLAY CONTROL UP/DOWN | 2 |

ULTRASONIC ARRAY TRANSDUCER TRANSCEIVER FOR A HAND HELD ULTRASONIC DIAGNOSTIC INSTRUMENT

This is a continuation-in-part of U.S. patent application Ser. No. 08/672,782, filed Jun. 28, 1996 now U.S. Pat. No. 5,722,412.

This invention was made with government support under agreement no. N00014-96-2-0002 awarded by the Office of Naval Research. The government has certain rights in the invention.

This invention relates to medical ultrasonic diagnostic systems and, in particular, to a fully integrated hand held ultrasonic diagnostic instrument.

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of analog and digital electronics, it is now possible to foresee a time when ultrasound systems will be able to be miniaturized to a size even smaller than their much earlier ancestors. The physician is accustomed to working with a hand held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

In accordance with the principles of the present invention, a diagnostic ultrasound instrument is provided which exhibits many of the features of a premium ultrasound system in a hand held unit. The instrument can be produced as a single unit or, in a preferred embodiment, the instrument is a two-part unit, one including a transducer, beamformer, and image processor and the other including a display and power source for both units. In such a configuration the transducer/processor unit can be manipulated with one hand while a cable between the two units enables the video to be shown on the display unit while the latter unit is held or positioned for optimal viewing of the ultrasound image. The cable also provides energy for the transducer/processor unit from the display unit.

In a preferred embodiment the ultrasound system, from the transducer through to a video output, is fabricated on four types of application specific integrated circuits (ASICs): a transmit/receive ASIC which is connected to the elements of an array transducer, a front end ASIC which performs and controls transmit and receive beamforming, a digital signal processing ASIC which provides processing of the ultrasound signals such as filtering, and a back end ASIC which receives processed ultrasound signals and produces ultrasound image data. A preferred architecture for an analog transmit/receive ASIC is a multiplexed N:1,1:M configuration. The image can be displayed on either a standard monitor or on a liquid crystal display (LCD). Comprised as it is of ASICs, the electronics of the unit can be fabricated on a few or even a single printed circuit board, eliminating the problems conventionally posed by connectors and cables. This sophisticated ultrasound instrument can be manufactured as a hand held unit weighing less than five pounds.

In the drawings:

FIGS. 3a and 3b are front and side views of the transducer unit of a two-unit hand-held ultrasound system of the present invention;

FIG. 4 illustrates the two units of a handheld ultrasound system of the present invention in a two-unit package;

FIG. 10 is a chart of the user controls of the ultrasound system of FIG. 1.

Figure 1:
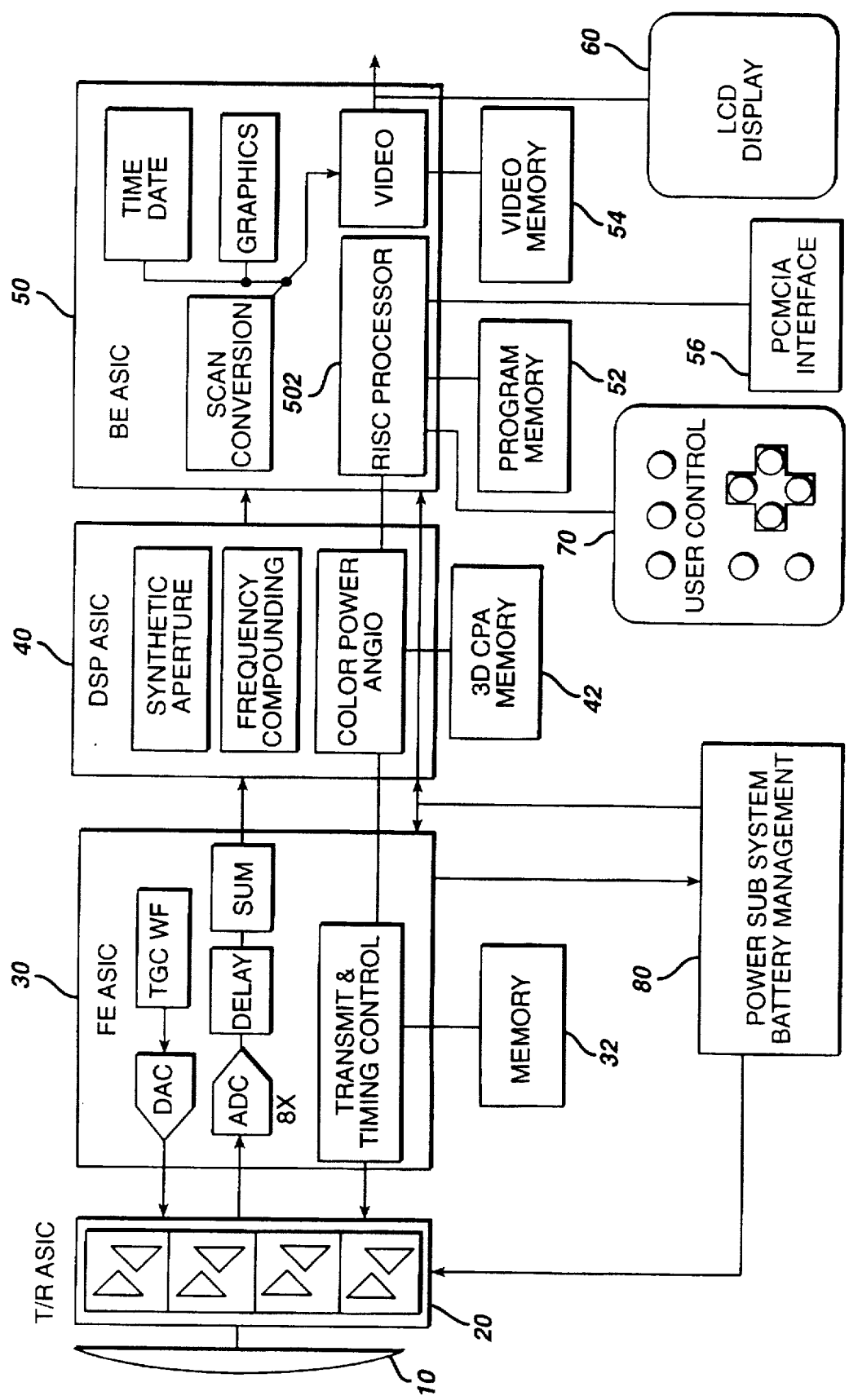
FIG. 1 illustrates in block diagram form the architecture of a hand-held ultrasound system of the present invention.

Referring first to FIG. 1, the architecture of a hand-held ultrasound system of the present invention is shown. It is possible to package an entire ultrasound system in a single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 30 also controls the transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which beamforms the echoes from the individual transducer elements into scanline signals. The front end ASIC controls the transmit waveform, timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformed scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding, Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as an infrared transmitter or a PCMCIA interface 56. This interface allows other modules and functions to be attached to or communicate with the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from a power subsystem 80. The power subsystem 80 includes a DC converter to convert the low battery voltage to a higher voltage which is applied to the transmit/receive ASIC 20 to drive the elements of the transducer array 10.

Figure 2B:
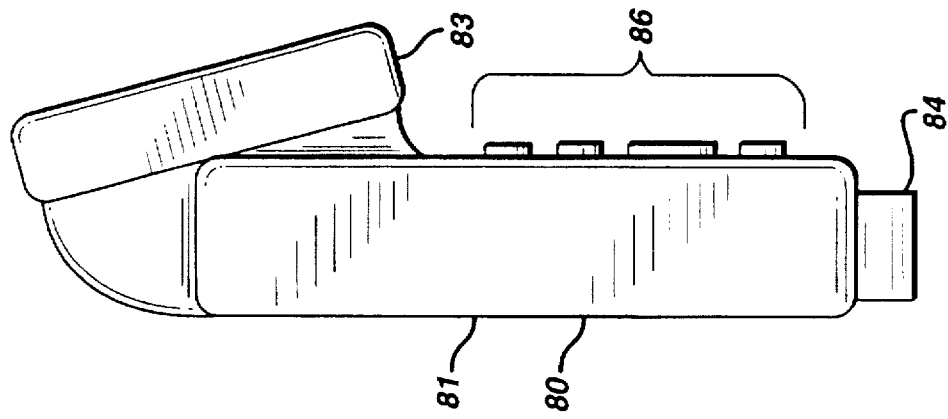
FIGS. 2a and 2b are front and side views of a hand-held ultrasound system of the present invention which is packaged as a single unit.
Figure 2A:
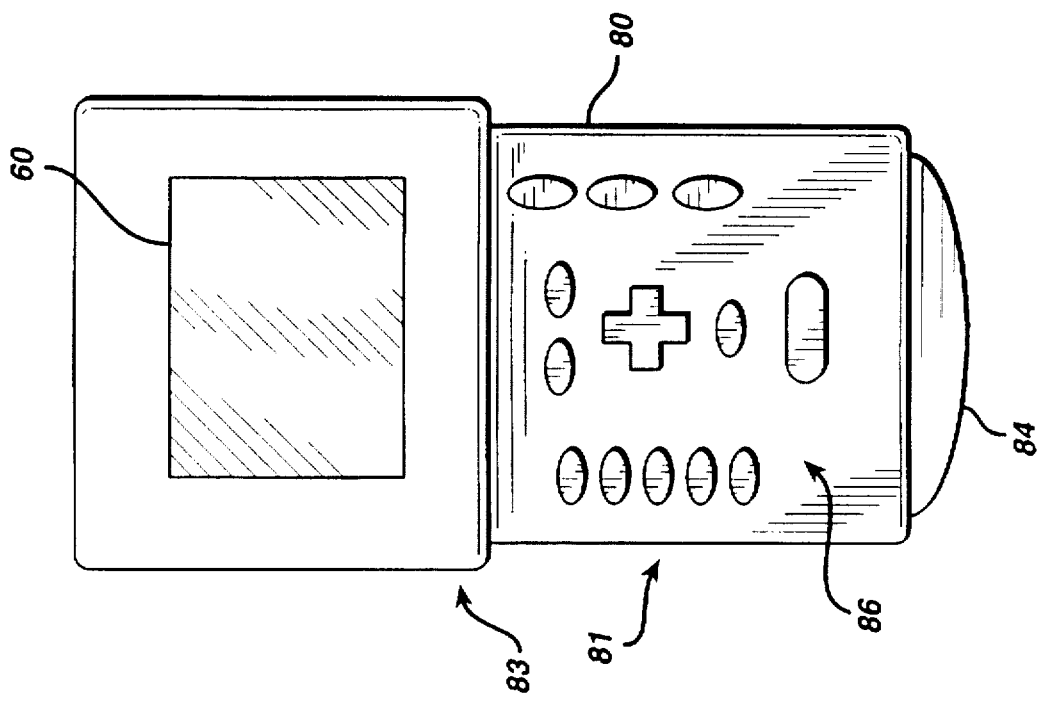

FIGS. 2a and 2b illustrate a one piece unit 80 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 80 is the aperture 84 of the curved transducer array 10. In use, the transducer aperture is held against the patient to scan the patient and the ultrasound image is displayed on the LCD display 60.

FIG. 2b is a side view of the unit 80, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

FIGS. 3 and 4 illustrate a second packaging configuration in which the ultrasound system is housed in two separate sections. A lower section 81 includes the transducer array, the electronics through to a video signal output, and the user controls. This lower section is shown in FIG. 3a, with the curved transducer array aperture visible at the bottom. The lower section is shown in the side view of FIG. 3b. This lower section measures about 11.4 cm high by 9.8 cm wide by 2.5 cm deep. This unit has approximately the same weight as a conventional ultrasound scanhead. This lower section is connected to an upper section 83 as shown in FIG. 4 by a cable 90. The upper section 83 includes an LCD display 82 and a battery pack 88. The cable 90 couples video signals from the lower unit 81 to the upper unit for display, and provides power for the lower unit from the battery pack 88. This two part unit is advantageous because the user can maneuver the lower unit and the transducer 84 over the patient in the manner of a conventional scanhead, while holding the upper unit in a convenient stationary position for viewing. By locating the battery pack in the upper unit, the lower unit is lightened and easily maneuverable over the body of the patient.

Other system packaging configurations will be readily apparent. For instance, the front end ASIC 30, the digital signal processing ASIC 40, and the back end ASIC 50 could be located in a common enclosure, with the beamformer of the front end ASIC connectable to different array transducers. This would enable different transducers to be used with the digital beamformer, digital filter, and image processor for different diagnostic imaging procedures. A display could be located in the same enclosure as the three ASICS, or the output of the back end ASIC could be connected to a separate display device.

Figure 5:
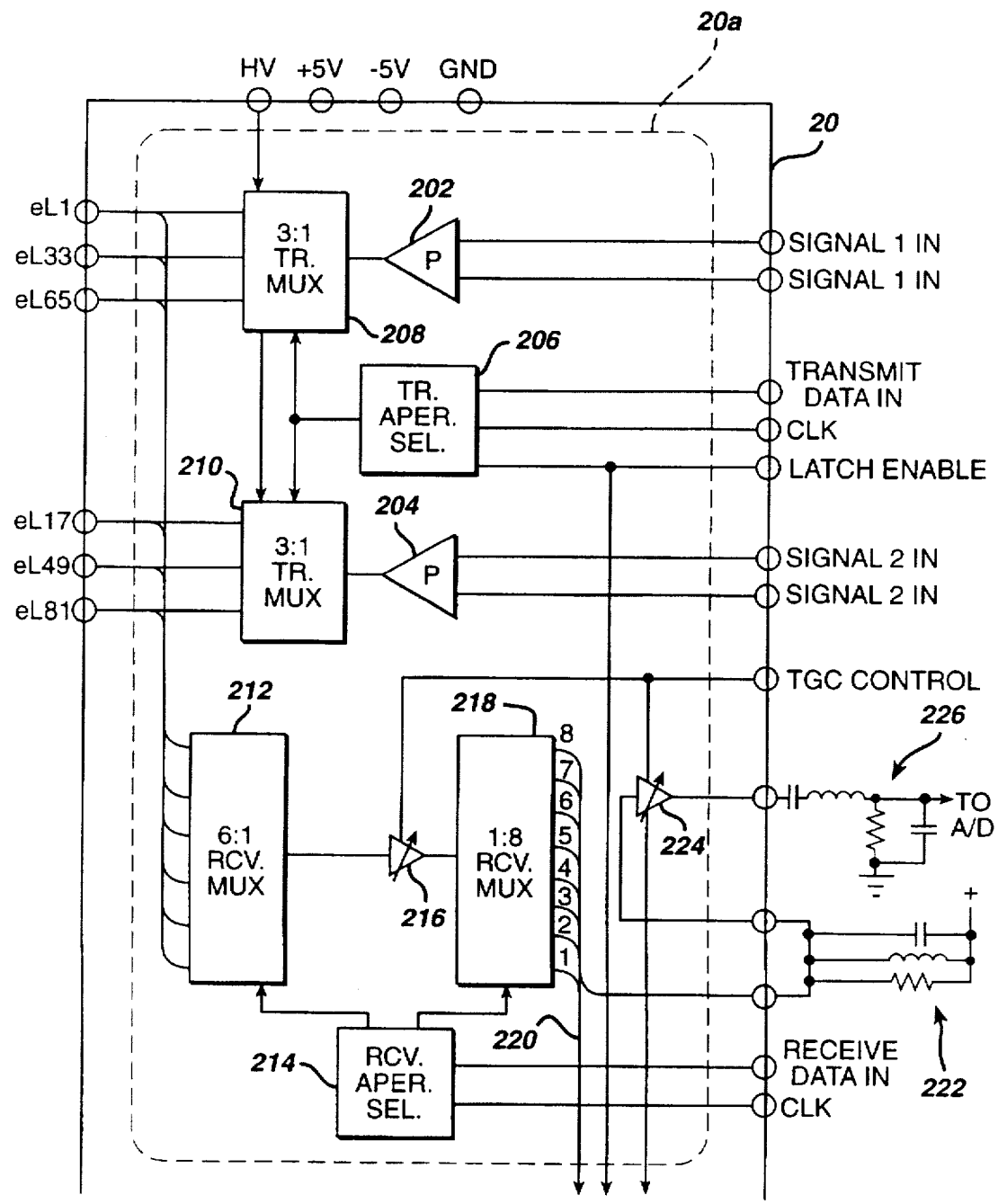
FIG. 5 is a schematic diagram of the transmit/receive ASIC of the ultrasound system of FIG. 1.

Referring now to FIG. 5, the transmit/receive ASIC 20 is shown in greater detail. This ASIC is comprised of sixteen sections, each of which is coupled to six transducer elements of the array 10. The illustrated section 20a is coupled to elements 1, 17, 33, 49, 65 and 81 at the terminals on the left side of the drawing. With six elements per section, the entire ASIC can operate with a 96 element transducer. Each section could be configured to operate with eight elements, in which case the ASIC could control a 128 element transducer, for instance. Prior to the transmission of an ultrasonic pulse for a scanline, a serial stream of data from the front end ASIC 30 is clocked into transmit aperture select logic 206 at the Transmit Data In terminal at the right side of the drawing. The transmit aperture select logic 206 uses this data to set multiplexer switches in 3:1 transmit muxes 208 and 210 for the transducer elements that will be active for the particular scanline. For instance, the next scanline to be transmitted may have a transmit aperture comprising elements 1–32. This requires that transmit mux 208 closes a switch to connect pulser 202 to the element 1 terminal, and the transmit mux 210 closes a switch to connect pulser 204 to the element 17 terminal. In a similar manner the transmit muxes in the other fifteen sections of the ASIC will connect pulsers to element terminals 2–16 and 18–32.

At the times when the connected elements 1 and 17 are to be activated, drive signals for the pulsers 202 and 204 are applied to the Signal 1 In and Signal 2 In terminals by the front end ASIC. For unipolar pulsers the drive signals are applied to single input terminals of each pulser. Alternatively, complementary waveforms are applied at the appropriate times to the paired terminals when bipolar drive signals are used, as illustrated by the paired input terminals for each pulser in this drawing. These drive signals are applied as logic level signals to the pulser inputs, then converted to high voltage driving waveforms by the application of high voltage HV applied to the muxes 208 and 210. It is also possible to fabricate the pulser and mux functions as a single unit, whereby each switch of the muxes is effectively a high voltage pulser. Stated another way, this means that each mux would comprise three separately controlled pulsers. Alternatively, the two pulsers at the inputs of the transmit muxes could be deleted and replaced by six pulsers at the outputs of the transmit muxes, however, the illustrated embodiment advantageously requires only two, low voltage pulsers. Continuing with the example of the aperture of elements 1–32, if element 1 is at the periphery of the aperture and element 17 is more central to the aperture, element 1 would be pulsed earlier in time than element 17 to produce a focused transmitted ultrasonic waveform.

Prior to transmission of the scanline a stream of digital data from the front end ASIC is clocked into receive aperture select logic 214 from the Receive Data In terminal connected to receive aperture select logic 214. The receive aperture select logic closes switches in a 6:1 receive mux 212 and a 1:8 receive mux 218 for the proper receive aperture. Like the transmit aperture select logic, the receive aperture select logic includes buffer storage so that data for the next scanline can be received while the ASIC is receiving echoes from the current scanline. The illustrated embodiment is designed for a sixteen element folded receive aperture as shown by the eight data bus lines at the output of the 1:8 receive mux 218. The inputs to the 6:1 receive mux 212 are connected to the six element terminals for section 20a and are protected from the high drive voltages by the integration of transmit/receive networks at the mux inputs. The receive aperture select logic 214 connects one of the inputs of the mux 212 to the mux output, and the received signal from the selected element is applied to a first time gain control (TGC) amplifier 216. The gain of this TGC amplifier is controlled by a control signal applied to a TGC Control terminal of the ASIC. The amplification provided by amplifier 216 increases as ultrasonic echoes are received from increasing depths, in the conventional manner. The amplified echo signals are then coupled by the switching of the 1:8 receive mux 218 to one of the data bus lines 220.

Each of the data bus lines 220 is coupled to the same corresponding output of every 1:8 receive mux on the ASIC. The outputs of the mux 218 are numbered from 1–8. Output 1 of each 1:8 receive mux is coupled to the same one of the data lines; output 2 of each 1:8 receive mux is coupled to another one of the data lines; and so forth. The preferred embodiment system uses a sixteen element folded aperture of scanlines transmitted orthogonal to the transducer. This means that two elements of the aperture will have the same receive phases of operation; the sixteen elements of the receive aperture will be paired to have eight receive phases. For instance, if the received scanline is located at the center of an aperture of elements 1–16, elements 1 and 16 will have the same receive timing. Echoes received by element 1 will be connected through mux 212, amplified by TGC amplifier 216, connected through mux 218 and produced as a current output at output 8 of the mux 218. At the same time, an echo received by element 16 will be connected through the muxes of another section of the ASIC, identically amplified by another TGC amplifier, and produced as a current output at output 8 of another 1:8 receive mux. These two currents are identically phased by virtue of the folded aperture, and combine on the data line which is coupled to output 8 of the receive muxes.

The currents on each data line are filtered and converted to voltages by a filter network such as that shown at 222. In the preferred embodiment filter network 222 is external to and coupled to a terminal of the ASIC so that its components and hence its filter characteristic can be easily selected and changed. The filter characteristic is a bandpass chosen to match the passband of the transducer. For a 3.5 MHz transducer the passband could extend from 1.5 to 5.5 MHz, for example. The filter is connected to a current source through the filter impedance to convert the current signals to a single voltage. This voltage reenters the ASIC through another (or the same) ASIC terminal and is applied to the input of a second TGC amplifier 224. The use of two TGC amplifiers enables operation over the wide dynamic range of the two cascaded amplifiers. In the illustrated embodiment a single TGC Control applies the same control characteristic to both TGC amplifiers 216 and 224, but it is also possible to apply separate and different TGC characteristics to the two amplifiers. The amplified echo signals are brought to a final output terminal of the ASIC where they are filtered by a bandpass filter 226 and coupled to an analog to digital (A/D) converter at the input of the beamformer on the front end ASIC.

The separate sections of the transmit/receive ASIC 20 may be contained in separate ASICs or combined so that several sections are integrated on the same ASIC. Preferably all sixteen sections are integrated onto a single ASIC chip.

Thus it is seen that, in the preferred embodiment, the transmit/receive ASIC 20 operates with a 96 element transducer array, and uses a 32 element transmit aperture and a 16 element folded receive aperture. With the use of a synthetic aperture as discussed below, the system exhibits a 32 element aperture on both transmit and receive.

Figure 6:
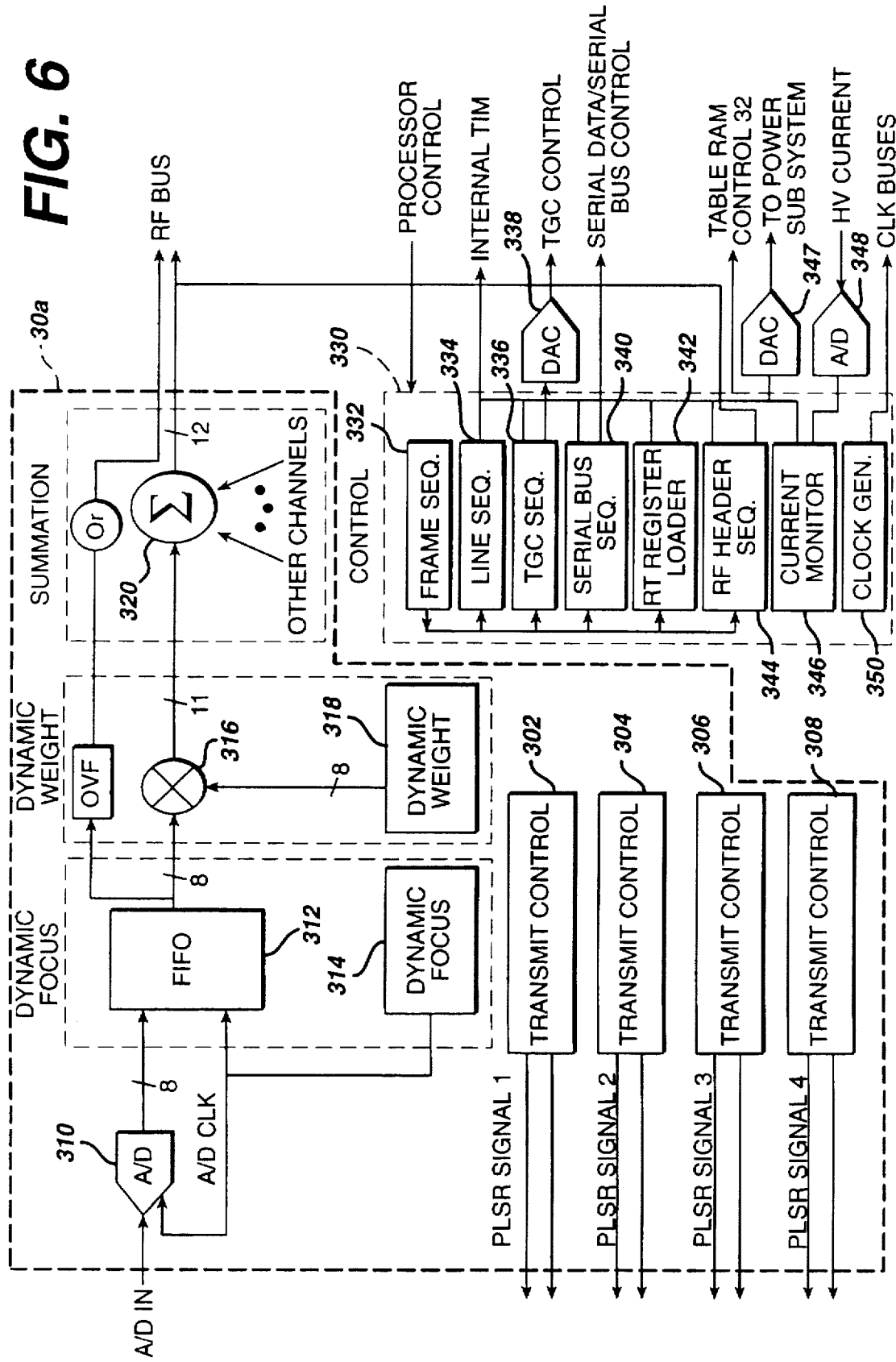
FIG. 6 is a block diagram of the front end ASIC of the ultrasound system of FIG. 1.

Details of the front end ASIC 30 are shown in FIG. 6. This drawing shows one section 30a of the front end ASIC 30. There are eight such sections on the front end ASIC to provide beamforming of the eight outputs from the transmit/receive ASIC 20. Each echo signal output is coupled to the input of an A/D converter 310, where the echo signals are converted to digital data. The digital data from each element (or each pair of elements in a folded aperture) is shifted into a first in, first out (FIFO) register 312 by a clock signal A/D CLK. The A/D CLK signal is provided by a dynamic focus timing circuit 314 which defers the start of the clock signal to provide an initial delay, then controls the signal sampling times to provide dynamic focusing of the received echo signals. The length of the FIFO register 312 is determined by the initial delay, the transducer center frequency, the aperture size, the curvature of the array, and the beam steering requirement. A higher center frequency and a curved array will reduce the steering delay requirement and hence the length of the FIFO register, for instance. The delayed echo signals from the FIFO register 312 are coupled to a multiplier 316 where the echo signals are weighted by dynamic weight values stored in a dynamic weight register 318. The dynamic weight values weight the echo signals in consideration of the effects of a dynamic receive aperture such as the number of active elements, the position of an element in the aperture, and the desired apodization function, as the aperture expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade by a summing circuit 320. The beamformed echo signals, together with synchronous overflow bits, are produced as output scanline data on an RF data bus. Accompanying each sequence of scanline echo signals is identifying information provided by an RF header sequencer on the ASIC, which identifies the type of scanline data being produced. The RF header can identify the scanline as B mode echo data or Doppler data, for instance.

Other digital storage devices can be used to provide the beamformer delays, if desired. A dual ported random access memory can be used to store the received digital echo samples, which are then read out from the memory at times or sequences which provide the desired delay for the signals from the transducer elements.

Each section 30a of the front end ASIC includes transmit control circuits 302–308 for four transducer elements of the array. The eight sections thus provide transmit control for 32 elements of the array at the same time, thereby determining the maximum transmit aperture. The transmit control circuits produce pulse waveforms at the desired transmission frequency and at the appropriate times to produce a transmitted acoustic signal which is focused at the desired depth of focus.

The front end ASIC includes a common control section 330 which provides overall realtime control for the transmission and receive functions. The control section 330 is controlled by and receives data under control of the RISC processor located on the back end ASIC. The data tables for a particular imaging mode are loaded into random access memory (RAM) 32 prior to scanning and are loaded into the control section 330 under command of the RISC processor. The control of scanning of individual lines is then controlled and varied in real time. The control section 330 includes a number of sequencers for the sequence of transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the scanlines which are transmitted and received in the proper sequence. In preparation for a new scanline the line sequencer controls the TGC sequencer 336 so that it will produce the desired sequence of TGC control data. The TGC control data from the TGC sequencer is converted to a voltage signal by a digital to analog converter (DAC) 338 and applied to the TGC Control input terminal(s) of the transmit/receive ASIC 20. The line sequencer 334 also controls the serial bus sequencer 340, which produces serial data on a serial bus for the transmit and receive aperture select logic circuits 206 and 214 on the transmit/receive ASIC. The receive/transmit (RT) register loader 342 controls the loading of data for a new scanline into various registers on both ASICs, including the aperture select logic circuits 206 and 214, the transmit control circuits 302–308, the dynamic focus timing circuit 314 and the dynamic weight register 318. All registers which perform real time functions are double buffered. As discussed above, the various registers are buffered so that the control data can be put on the serial bus and loaded into the various registers during the line preceding the scanline for which the control data is used.

The front end ASIC 30 includes a current monitor circuit 346, which samples the current on the HV bus by way of an A/D converter 348. The current monitor assures patient safety by reducing or completely shutting down the high voltage supply if excessive current levels are detected, thereby protecting the patient from an overheated transducer or unacceptably high acoustic output levels. The current monitor circuit may also be located in the power and battery management sub system 80.

The front end ASIC includes in its control section a clock generator 350 which produces a plurality of synchronous clock signals from which all operations of the system are synchronized. To prevent interference and crosstalk among the closely spaced devices of the system, the video output signal frequency is synchronized to a clock signal of the clock generator, so harmonics of one frequency will not produce interfering components in the other. A crystal oscillator (not shown) is coupled to the front end ASIC 30 to provide a basic high frequency such as 60 MHz from which all of the clock signals of the system may be derived.

Figure 7:
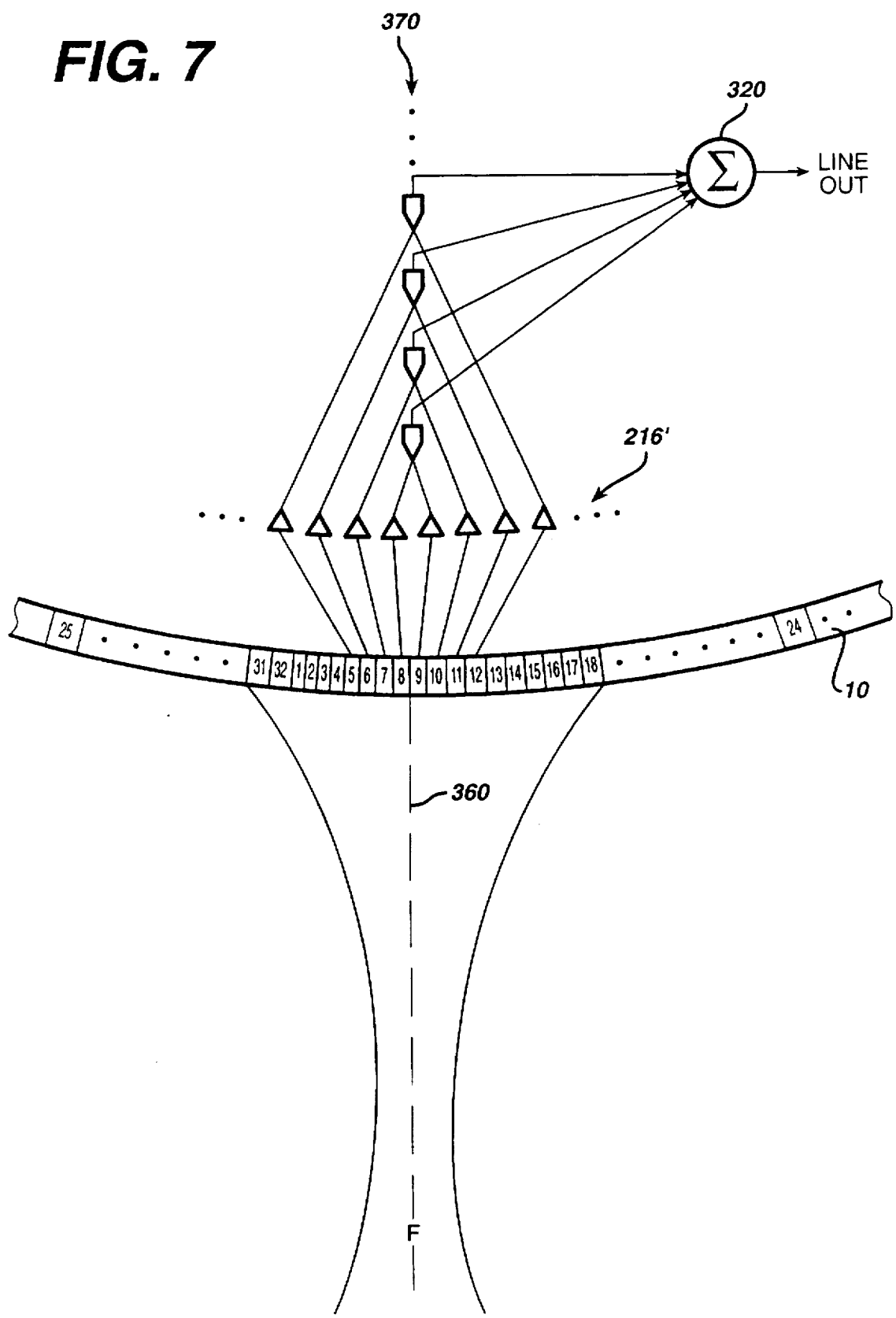
FIG. 7 illustrates the aperture control afforded by the transmit/receive and front end ASICs.

The operation of the transmit/receive and front end ASICs 20 and 30 to produce a synthetic folded aperture scanline from 32 elements of a curved array is illustrated with reference to FIG. 7. In this drawing the ASICs are controlling an aperture of the transducer comprising 32 elements numbered from 25 through 32, then 1 through 24 of the curved array 10. Gathering the full aperture of scanline information requires two transmit sequences of all 32 elements. To transmit, the line sequencer 334, the serial bus sequencer 340, and the RT register loader 342 load the proper transmit mux data into the sixteen transmit aperture select logic circuits 206 and the 32 transmit controllers on the front end ASIC. The aperture select logic then control the 32 transmit muxes to connect pulsers to elements numbered 25–32 and 1–24, the desired transmit aperture. The pulsers are pulsed by the transmit control circuits so as to produce an acoustic wave which is focused at point F in FIG. 7.

Following the first pulse transmission, echoes are received by the center group of elements numbered 1–16, which at that time are connected by the sixteen 6:1 receive muxes and 1:8 receive muxes to eight output data lines. The sixteen receive signals are shown as separate when they pass through the initial TGC amplifiers, eight of which are shown in a row as indicated at 216' in FIG. 7. The like phased signals are then seen to combine in pairs by virtue of the folded aperture where pairs of lines come together at the input of the beamformer delay lines, four of which are shown as indicated at 370. In the illustrated example the scanline 360 extends from the center of the array aperture between elements 8 and 9. This means that echo signals received by elements 8 and 9 will be in phase, and can be combined. Likewise, echoes received by paired elements 7 and 10, paired elements 6 and 11, and paired elements 5 and 12 can also be combined. Thus, following the first transmitted pulse, echoes received by elements 1–16 are delayed by the eight delay FIFOs and summed by the summing circuit 320. This half aperture is then stored for receipt of the other half aperture.

Another acoustic pulse is transmitted by all 32 elements of the aperture. After this second pulse, the receive muxes now connect echoes from elements 25–32 and 17–24 to the beamformer. By virtue of the folded aperture symmetry the echoes from element 32 are paired with echoes from element 17 and the two are combined. Likewise, echoes from element 31 are paired with echoes from element 18, and so forth, out to the most lateral paired elements 25 and 24.

The sixteen received echoes, paired to eight signals by the folded aperture, are appropriately delayed by the eight delay FIFOs and summed to form a second half aperture of the scanline. The two halves of the aperture are now summed as a function of the location of the echo components along the scanline of the two sequences. Thus, the complete aperture has been formed by combining the separate receptions of echoes from the inner sixteen elements of the aperture, then from the outer sixteen elements. A precisely beamformed synthetic aperture signal is produced by maintaining identical conditions of TGC control during both reception intervals. The dynamic weighting and dynamic focusing affect the two reception sequences differently by reason of the differing aperture locations of the receiving elements during the two sequences. The delays applied by the FIFOs during the two sequences will be different by reason of the differing locations across the aperture of the receiving elements from one sequence to the next.

Figure 8:
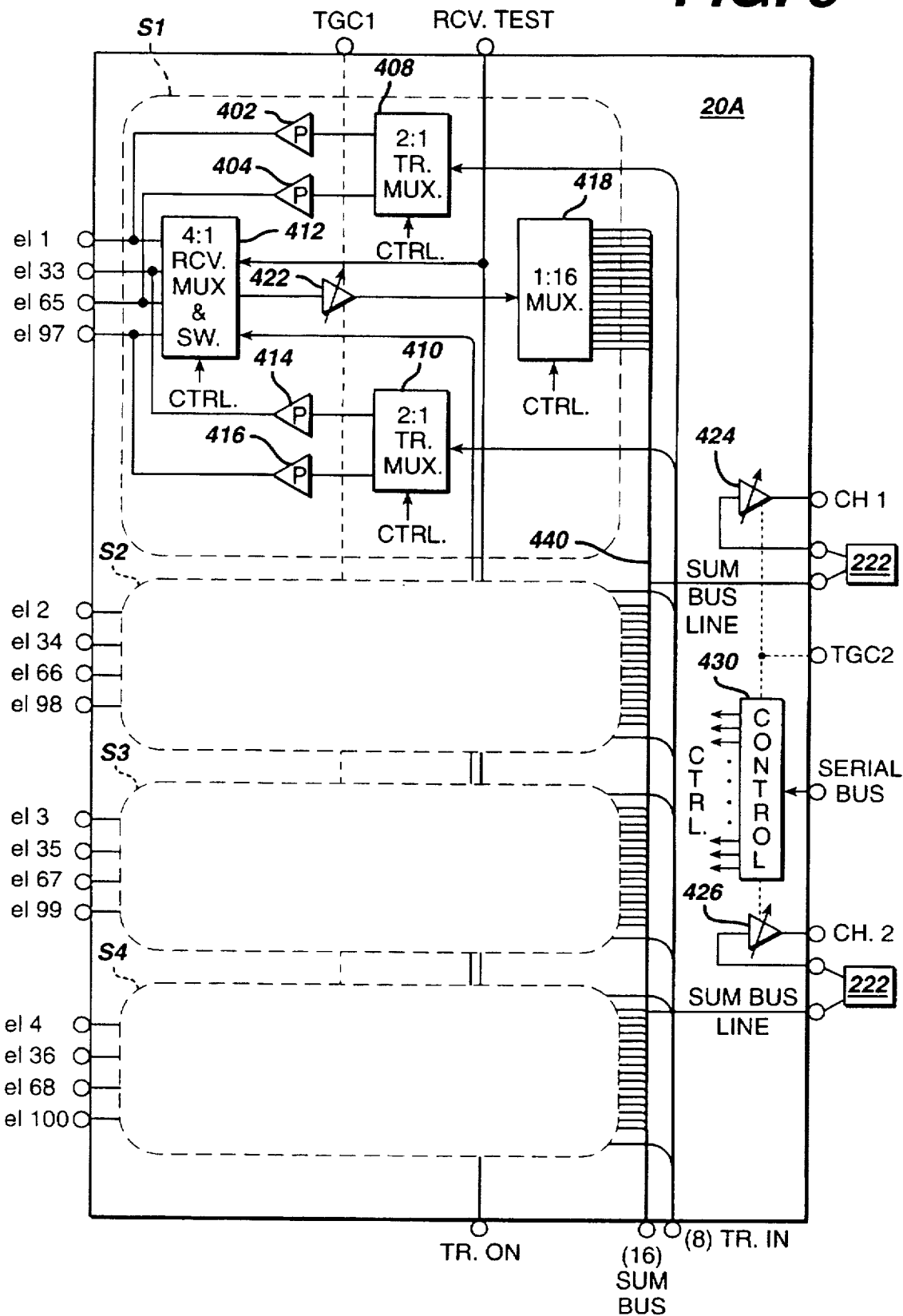
FIG. 8 illustrates in block diagram form a second embodiment of the present invention.

A preferred transmit/receive ASIC 20A is shown in FIG. 8. The signal paths of the ASIC 20A are divided into four identical sections S1, S2, S3, and S4. In this drawing section S1 is shown in internal detail. The section S1 includes two 2:1 transmit multiplexers 408 and 410, each of which is responsive to a pulser signal on one of eight (8) Transmit In lines. Each 2:1 Transmit Multiplexer has two outputs which drive pulsers 402, 404, and 414, 416, the outputs of which are coupled to ASIC pins to which transducer elements are connected. In the illustrated embodiment the 2:1 Transmit Multiplexer 408 is coupled to drive either element 1 or element 65, and the 2:1 Transmit Multiplexer 410 is coupled to drive either element 33 or element 97. The 2:1 Transmit Multiplexers of the other sections of the ASIC are each similarly coupled to four transducer elements. With a separate pulser for each transducer element, the ASIC 20A can independently and simultaneously drive eight of the sixteen transducer elements to which it is connected.

The transducer element pins to which the pulsers of each section are coupled are also coupled to the inputs of a 4:1 Receive Multiplexer and Switch 412. When the pulsers are driving the transducer elements during ultrasound transmission, a signal on a Transmit On line which is coupled to all of the 4:1 Receive Multiplexers and Switches on the ASIC switches them all into a state which presents a high impedance to the high voltage drive pulses, thereby insulating the rest of the receive signal paths from these high voltage pulses. All of the 4:1 Receive Multiplexers and Switches of the ASIC are also coupled to a Receive Test pin of the I.C., by which a test signal can be injected into the receive signal paths and propagate through the receiver system. During echo reception each 4:1 Receive Multiplexer and Switch couples the signals of one of the four transducer elements to which it is coupled to a 1:16 Multiplexer 418 by way of a first TGC stage 416. The gain of the first TGC stages on the ASIC is controlled by a voltage applied to a TGC1 pin of the ASIC which, in a constructed embodiment, comprises two pins for application of a differential control voltage. The 1:16 Multiplexers of each section of the ASIC each route received echo signals to one of the sixteen (16) lines of a Sum Bus 440. Two of the sixteen Sum Bus lines are shown at the right side of the drawing, and are coupled to filter circuits 222. The filtered bus signals are coupled to input pins leading to two second TGC stages 424 and 426, the gain of which is controlled by the voltage applied to one or two TGC2 pins. The outputs of these second TGC stages in the illustrated embodiment are connected to output pins leading to channels 1 and 2 of the ultrasound system's beamformer.

The ASIC 20A also includes a control register 430 which receives control signals over a serial bus from the beamformer. The control register distributes control signals to all of the multiplexers of the ASIC as shown by the Ctrl. input arrows.

A constructed embodiment of ASIC 20A will have a number of pins for supply and bias voltages and ground connections and are not shown in the drawing.

Figure 9:
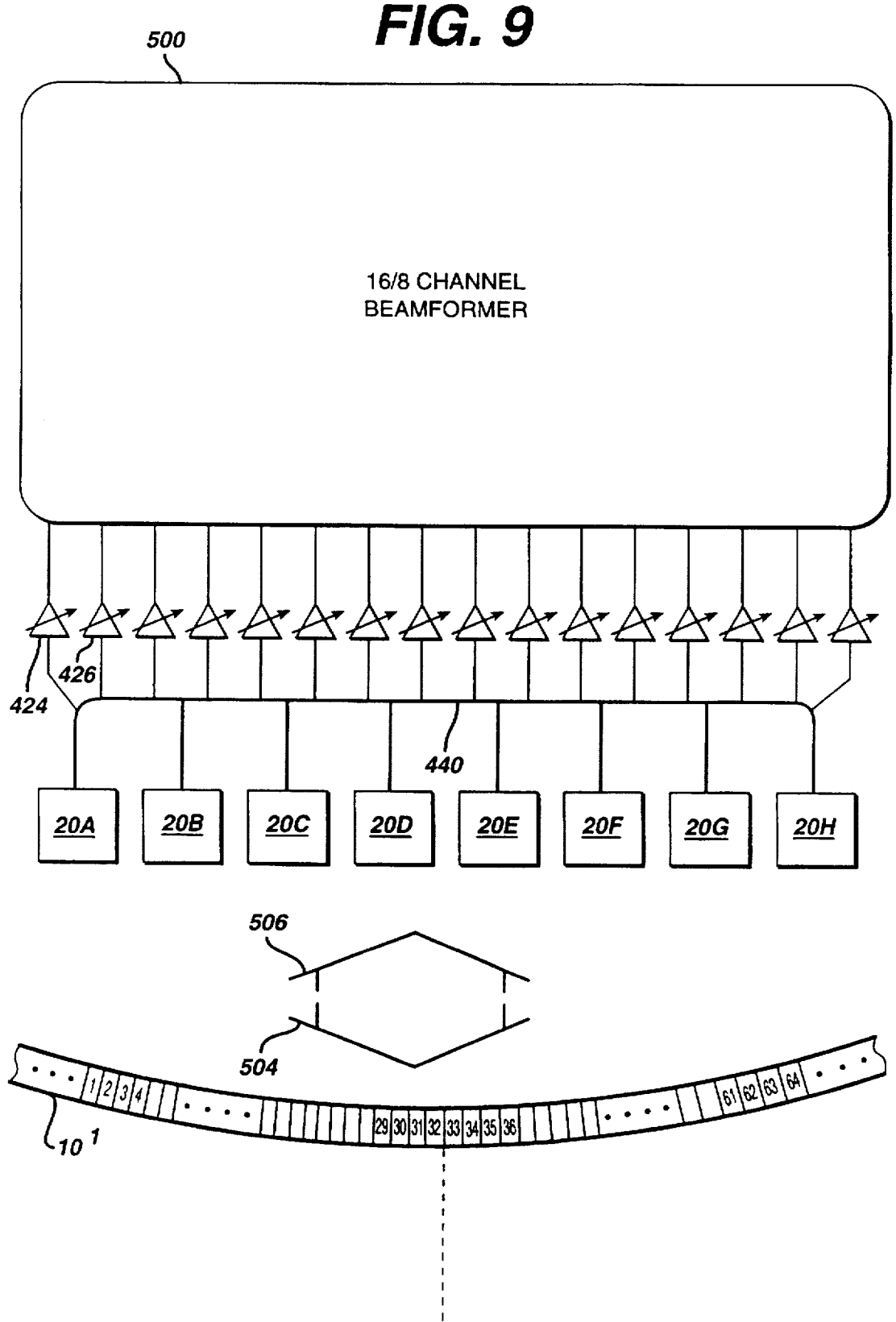
FIG. 9 illustrates the ASIC of FIG. 8 connected to a transducer array and a beamformer.

A system using the ASICs of the present invention exhibits an N:1.1:M architecture, where N is the number of transducer elements divided by the maximum aperture size, and M is the number of beamformer channels. These ASICs can be used to connect a wide variety of transducer arrays of various numbers of elements to beamformers of different numbers of channels in numerous ways. An example of this versatility is shown in the system of FIG. 9, which shows a transducer 10' coupled (as indicated by arrows 506,504) to eight ASICs 20A-20H, the Sum Bus 440 of which is coupled by the sixteen second TGC stages of the ASICs to a sixteen channel beamformer 500. (For clarity of illustration the second TGC stages are separately illustrated, although they are in fact integrated on the ASICs.) In this example the eight ASICs, each having sixteen pins for connection to transducer elements, are connected to separately drive all 128 elements of transducer array 10'. The 2:1 Transmit Multiplexers of the eight ASICs are capable of driving 64 elements at once, and thus can operate the transducer array to have a 64 element transmit aperture, represented by transducer element 1–4 ... 29–36 ... 61–64 in the drawing. This 64 element aperture is centered between elements 32 and 33. This arrangement is capable of driving all of the elements of a 64 element aperture for each transmitted ultrasound wave. The control registers of the eight ASICs 20A-20H can be conveniently coupled to separate lines of an eight line data bus from the beamformer, each line serving as a serial bus for a particular control register, thereby enabling all eight control registers to be loaded simultaneously.

Echo signal reception over the full 64 element aperture can be accomplished in several ways. One is to employ a folded and synthetic aperture as described in FIG. 7. After a first wave transmission the echoes on elements 17–32 are received and folded together with the echoes from elements 48–33. That is, one Sum Bus line would have the echoes from elements 17 and 48 multiplexed onto it, another Sum Bus line would have the echoes from elements 18 and 47 multiplexed onto it, and so forth. These sixteen folded signals are appropriately delayed and combined to develop a focused signals. After a second wave transmission the outer elements of the aperture are used for folded reception, delayed and combined with each other and the first focused signals to complete the aperture.

This N:1.1:M ASIC architecture can be used with an eight channel beamformer 500 in place of the 16 channel beamformer by use of the folded and synthetic aperture techniques, or by use of a coarse aperture reception technique, as described in U.S. Pat. No. 4,542,653. In this technique, adjacent elements which were independently excited during beam transmission are paired during reception by combining their received signals and using the same focusing delay for them. Effectively, this means that the transducer pitch is coarser during reception by a factor of two. While this will raise the level of the grating lobes of the received beam pattern, the combined transmit and receive beam patterns will still be acceptable, and the system will benefit by the higher sensitivity of a larger receive aperture. If the grating lobes should prove objectionable, they can be reduced by using an aperiodic aperture, in which the number of elements combined as groups vary from group to group across the aperture. The aperiodic aperture will effectively blend the grating lobe effects into a uniform image background.

In one such arrangement the signals received by four transducer elements are directed to the same Sum Bus line, by suitably programming the 1:16 Multiplexers, for application to the inputs of each of eight beamformer channels. This allows the received signals from elements 17 and 18 to be combined with the received signals from elements 47 and 48 on the same Sum Bus line, and all four signals coupled to the input of one beamformer channel. Thus, both coarse receive and folded aperture techniques are employed simultaneously. A thirty-two element aperture can be received following a single transmitted wave, or a sixty-four element aperture formed by the synthetic aperture technique with two wave transmissions. If only a fine receive aperture is used, the receive aperture is restricted to thirty-two elements with use of the folded and synthetic aperture techniques, or sixteen elements with the folded or synthetic aperture techniques alone.

The front end ASIC of FIG. 6 is seen to have four transmit control circuits for each receive channel, a total of 32 transmit control circuits in all. These 32 transmit control circuits can be coupled to the sixty-four pulser inputs of the eight transmit/receive ASICS of FIG. 9 by coupling one transmit control circuit to both inputs of each pair of Transmit Multiplexers 408,410 and programming one of the Transmit Multiplexers to be enabled and the other disabled through the control signals of the control register 430. This effectively converts each pair of 2:1 Transmit Multiplexers to operation as a 4:1 Transmit Multiplexer, giving a maximum transmit aperture of thirty-two independently controlled elements.

The foregoing examples apply to a received beam that is directed orthogonal to the center of the aperture of the array. If the received beam is to be steered off the orthogonal line as well as focused, the folded aperture technique cannot be used, since varying delays have to be employed across the full active aperture.

Variations of the ASIC 20A will also be apparent to those skilled in the art. If all of the transducer elements are to be driven simultaneously and independently, the 2:1 Transmit Multiplexers can be eliminated and the pulsers 402,404,414, 416 driven directly. The 1:16 Multiplexers could be expanded to 1:32 for a thirty-two channel beamformer, which could control 64 element apertures through the folded and coarse aperture techniques with no degradation in the frame rate. The 4:1 Receive Multiplexers and Switches could be partitioned into two 2:1 Receive Multiplexers and Switches, each coupled to its own bus multiplexer. Such variations will accommodate different apertures for operation at different and higher image frame rates.

The back end ASIC 50 is the location of the RISC processor 502, which is used to coordinate the timing of all of the operations of the handheld ultrasound system. The RISC processor is connected to all other major functional areas of the ASICs to coordinate processing timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator on the front end ASIC 30. The RISC processor also communicates through an infrared beam interface, by which the processor can access additional program data or transmit image information remotely. The infrared interface can connect to a telemetry link for the transmission of ultrasound images from the handheld unit to a remote location, for instance. A PCMCIA data interface may also or alternately be employed for data communication, as desired.

The RISC processor is operated under user control by commands and entries made by the user on the user control 70. A chart showing control functions, the type of controls, and their description is shown in FIG. 10. It will be appreciated that a number of functions, such as patient data entry, Cineloop operation, and 3D review, will operate through menu control to minimize the number of key or button controls on the small handheld unit. To further simplify the unit a number of operating functions are preprogrammed to specific diagnostic applications and will operate automatically when a specific application is selected. Selection of B mode imaging will automatically invoke frequency compounding and depth dependent filtering, for instance, while a four multiplier filter will automatically be set up as a wall filter when Doppler operation is selected. The menu selection of specific clinical applications can automatically invoke specific feature settings such as TGC control characteristics and focal zones, for example.

What is claimed is:

1. An ultrasound system comprising:
   an enclosure;
   an array transducer located in said enclosure and accessing a patient through an acoustic window;
   a transceiver integrated circuit, connected to a plurality of the elements of said array transducer, for exciting said elements to transmit ultrasonic waves and receiving echoes from said elements; and
   a beamformer, coupled to said transceiver integrated circuit, for controlling the transmission of ultrasonic waves by said array transducer and delaying and combining echo signals received by said elements of said array transducer to form an ultrasonic beam.

2. The ultrasound system of claim 1, wherein said beamformer is fabricated on an integrated circuit.

3. The ultrasound system of claim 1, wherein said transceiver integrated circuit further includes a time gain control circuit coupled to receive echo signals for controlling the gain applied to said echo signals during the time of reception of a scanline of echoes.

4. The ultrasound system of claim 1, further comprising bandpass filter circuitry coupled to filter echo signals received by said elements of said array transducer.

5. The ultrasound system of claim 4, wherein said bandpass filter circuitry further comprises means for converting echo current signals to echo voltage signals.

6. The ultrasound system of claim 1, wherein said transceiver integrated circuit includes transducer element drivers responsive to said beamformer for selectively exciting said transducer elements, and a multiplexer circuit, coupled to said transducer element drivers, said transducer elements, and said beamformer for alternately causing said transducer elements to be excited by said drivers and to receive echo signals for said beamformer.

7. The ultrasound system of claim 6, wherein said multiplexer circuit comprises a transmit multiplexer coupled between a transducer element driver and a plurality of said transducer elements for coupling excitation signals from said driver to a selected one of said transducer elements, and a receive multiplexer coupled between a plurality of transducer elements and said beamformer for coupling an echo signal received by one of said transducer elements to said beamformer.

8. The ultrasound system of claim 7, further comprising a plurality of transmit multiplexers, each coupled between a transducer element driver and a plurality of said transducer elements for coupling excitation signals from respective drivers to selected transducer elements, wherein said transmit multiplexers are responsive to transducer aperture selection signals for determining the transmit aperture of said array transducer.

9. The ultrasound system of claim 8, wherein said array transducer has a plurality of transmit apertures each formed by a group of adjacent transducer elements, wherein each element of a group of said adjacent transducer elements is coupled to a different one of said plurality of transmit multiplexers, whereby said transducers of a group are all excited by means of said plurality of transmit multiplexers during an ultrasonic wave transmission sequence.

10. The ultrasound system of claim 8, further including a data storage device, coupled to said transmit multiplexers, for receiving said transducer aperture selection signals for one transmit beam while echo signals of a previously transmitted beam are being received.

11. The ultrasound system of claim 7, further comprising a plurality of receive multiplexers each coupled between a plurality of transducer elements and said beamformer, wherein said receive multiplexers are responsive to transducer aperture selection signals for coupling echo signals received by selected ones of said transducer elements to said beamformer to be combined in an ultrasound beam.

12. The ultrasound system of claim 11, wherein said array transducer has a plurality of receive apertures each formed by a group of adjacent transducer elements, wherein each element of a group of said adjacent transducer elements is coupled to a different one of said plurality of receive multiplexers, whereby echo signals received by the transducers of a group are all coupled by means of said plurality of receive multiplexers to said beamformer during reception of an ultrasonic scanline.

13. The ultrasound system of claim 11, further including a data storage device, coupled to said receive multiplexers, for receiving said transducer aperture selection signals for one scanline while echo signals of a previously transmitted scanline are being received.

14. The ultrasound system of claim 11, wherein said receive multiplexers are connected to form a folded receive aperture.

15. The ultrasound system of claim 14, wherein pairs of said receive multiplexers are coupled to different transducer elements which are to receive echo signals of the same receive phase; and wherein the echo signals received by the two receive multiplexers of each pair are combined prior to being delayed in beam formation.

16. A handheld ultrasound device comprising:
an enclosure;
an array transducer located in said enclosure and accessing a patient through an acoustic window;
a transceiver circuit, mounted in said enclosure and connected to the elements of said array transducer, for exciting said elements to transmit ultrasonic waves and receiving echoes from said elements, wherein said transceiver circuit is fabricated on an integrated circuit;
a beamformer, mounted in said enclosure and coupled to said transceiver circuit, for controlling the transmission of ultrasonic waves by said array transducer and delaying and combining echo signals received by said elements of said array transducer to form an ultrasonic beam, wherein said beamformer is fabricated on an integrated circuit;

wherein said transceiver circuit includes transducer element drivers responsive to said beamformer for selectively exciting said transducer elements, and a multiplexer circuit, coupled to said transducer element drivers, said transducer elements, and said beamformer for alternately causing said transducer elements to be excited by said drivers and to receive echo signals for said beamformer.

17. The handheld ultrasound device of claim 16, wherein said multiplexer circuit comprises a transmit multiplexer coupled between a transducer element driver and a plurality of said transducer elements for coupling excitation signals from said driver to a selected one of said transducer elements, and a receive multiplexer coupled between a plurality of transducer elements and said beamformer for coupling an echo signal received by one of said transducer elements to said beamformer.

18. The handheld ultrasound device of claim 17, further comprising a plurality of transmit multiplexers, each coupled between a transducer element driver and a plurality of said transducer elements for coupling excitation signals from respective drivers to selected transducer elements, wherein said transmit multiplexers are responsive to transducer aperture selection signals for determining the transmit aperture of said array transducer.

19. The handheld ultrasound device of claim 18, wherein said array transducer has a plurality of transmit apertures each formed by a group of adjacent transducer elements, wherein each element of a group of said adjacent transducer elements is coupled to a different one of said plurality of transmit multiplexers, whereby said transducers of a group are all excited by means of said plurality of transmit multiplexers during an ultrasonic wave transmission sequence.

20. The handheld ultrasound device of claim 18, further including a data storage device, coupled to said transmit multiplexers, for receiving said transducer aperture selection signals for one transmit beam while echo signals of a previously transmitted beam are being received.

21. The handheld ultrasound device of claim 17, further comprising a plurality of receive multiplexers each coupled between a plurality of transducer elements and said beamformer, wherein said receive multiplexers are responsive to transducer aperture selection signals for coupling echo signals received by selected ones of said transducer elements to said beamformer to be combined in an ultrasound beam.

22. The handheld ultrasound device of claim 21, wherein said array transducer has a plurality of receive apertures each formed by a group of adjacent transducer elements, wherein each element of a group of said adjacent transducer elements is coupled to a different one of said plurality of receive multiplexers, whereby echo signals received by the transducers of a group are all coupled by means of said plurality of receive multiplexers to said beamformer during reception of an ultrasonic scanline.

23. The handheld ultrasound device of claim 21, further including a data storage device, coupled to said receive multiplexers, for receiving said transducer aperture selection signals for one scanline while echo signals of a previously transmitted scanline are being received.

24. The handheld ultrasound device of claim 21, wherein said receive multiplexers are connected to form a folded receive aperture.

25. The handheld ultrasound device of claim 24, wherein pairs of said receive multiplexers are coupled to different transducer elements which are to receive echo signals of the same receive phase; and wherein the echo signals received by the two receive multiplexers of each pair are combined prior to being delayed in beam formation.

26. A handheld ultrasound device comprising:

an enclosure;

an array transducer located in said enclosure and accessing a patient through an acoustic window;

a transceiver circuit, mounted in said enclosure and connected to the elements of said array transducer, for exciting said elements to transmit ultrasonic waves and receiving echoes from said elements; and a beamformer, mounted in said enclosure and coupled to said transceiver circuit, for controlling the transmission of ultrasonic waves by said array transducer and delaying and combining echo signals received by said elements of said array transducer to form an ultrasonic beam, wherein said beamformer is fabricated on an integrated circuit;

wherein said beamformer is fabricated on an integrated circuit; and wherein said transceiver circuit includes a high voltage multiplexer circuit, responsive to said beamformer and coupled to said transducer elements, for causing said transducer elements to be excited to transmit ultrasonic waves.

27. A handheld ultrasound device comprising:

an enclosure;

an array transducer located in said enclosure and accessing a patient through an acoustic window;

a transceiver circuit, mounted in said enclosure and connected to the elements of said array transducer, for exciting said elements to transmit ultrasonic waves and receiving echoes from said elements; and a beamformer, mounted in said enclosure and coupled to said transceiver circuit, for controlling the transmission of ultrasonic waves by said array transducer and delaying and combining echo signals received by said elements of said array transducer to form an ultrasonic beam;

wherein said transceiver circuit is fabricated on an integrated circuit;

wherein said transceiver circuit further includes a time gain control circuit coupled to receive echo signals for controlling the gain applied to said echo signals during the time of reception of a scanline of echoes; and wherein said time gain control circuit comprises first and second cascaded TGC amplifiers.

28. A handheld ultrasound device comprising:

an enclosure;

an array transducer located in said enclosure and accessing a patient through an acoustic window;

a transceiver circuit, mounted in said enclosure and connected to the elements of said array transducer, for exciting said elements to transmit ultrasonic waves and receiving echoes from said elements; and a beamformer, mounted in said enclosure and coupled to said transceiver circuit, for controlling the transmission of ultrasonic waves by said array transducer and delaying and combining echo signals received by said elements of said array transducer to form an ultrasonic beam;

wherein said transceiver circuit is fabricated on an integrated circuit;

further comprising bandpass filter circuitry coupled to said transceiver circuit integrated circuit to filter echo signals received by said elements of said array transducer.

29. An ultrasound system comprising:

an enclosure;

an array transducer located in said enclosure and accessing a patient through an acoustic window; and a transceiver integrated circuit having a plurality of low voltage inputs, and a plurality of high voltage outputs connected to a plurality of the elements of said array transducer, and including a plurality of transducer drivers and multiplexers, responsive to signals at said low voltage inputs and coupled to said high voltage outputs, for exciting selected ones of said elements to transmit ultrasonic waves.

30. The ultrasound system of claim 29, wherein said array transducer comprises a curved linear array transducer.

31. The ultrasound system of claim 29, wherein said transducer drivers have inputs coupled to said low voltage inputs and outputs coupled to said multiplexers; and wherein said multiplexers have outputs coupled to said high voltage outputs.

32. The ultrasound system of claim 29, wherein said multiplexers have inputs coupled to said low voltage inputs and outputs coupled to said transducer drivers; and wherein said transducer drivers have outputs coupled to said high voltage outputs.

33. An ultrasonic imaging system, including an array transducer, a beamformer, and a transmit/receive integrated circuit coupled to said array transducer and said beamformer for multiplexing excitation signals to elements of said transducer array and echo signals from elements of said transducer array to channels of said beamformer comprising:

a plurality of transmit multiplexers, located on said integrated circuit, responsive to excitation command signals, and having outputs coupled to individual ones of said transducer elements, for selectively exciting elements of said array transducer;

an echo data bus located on said integrated circuit and coupled to channels of said beamformer; and a plurality of receive multiplexers, located on said integrated circuit, coupled to individual ones of said transducer elements, and having outputs coupled to said echo data bus, for selectively steering echo signals received by said transducer elements to channels of said beamformer.

34. The ultrasonic imaging system of claim 33, further comprising a plurality of TGC amplifiers, located on said integrated circuit for variably amplifying received echo signals.

35. The ultrasonic imaging system of claim 33, further comprising a control register located on said integrated circuit and coupled to said multiplexers for applying control signals to said multiplexers.

36. The ultrasonic imaging system of claim 33, further comprising one or more of said transmit/receive integrated circuits coupled to said array transducer and said beamformer and exhibiting an N:1.1:M architecture, where N is the number of elements of said transducer array divided by the number of elements of an aperture of said transducer array, and M is the number of channels of the beamformer.

37. The ultrasonic imaging system of claim 36, wherein said transducer array has 128 elements.

38. The ultrasonic imaging system of claim 37, wherein M is an integer multiple of eight.

39. The ultrasonic imaging system of claim 38, wherein M is equal to sixteen.

40. The ultrasonic imaging system of claim 38, wherein the number of transducer elements forming an aperture is 64.

41. The ultrasonic imaging system of claim 33, further comprising means for steering the echo signals received by two of said transducer elements to a common line of said data bus.

42. The ultrasonic imaging system of claim 41, wherein said means for steering comprises means for forming a folded aperture for beamforming.

43. The ultrasonic imaging system of claim 41, wherein said means for steering comprises means for combining the echo signals received by adjacent transducer elements prior to beamforming.

44. The ultrasonic imaging system of claim 33, further comprising means for controlling said transmit multiplexers to form a fine pitch transmit aperture, and means for controlling said receive multiplexers to form one or more of a coarse pitch receive aperture, a folded aperture, or a synthetic aperture.

45. In an ultrasonic diagnostic imaging system, including an ultrasonic array transducer having a plurality of transducer elements, a transmit/receive integrated circuit for controlling the transmission of ultrasonic waves by said transducer and responding to the reception of echo signals by said transducer comprising:

a plurality of transducer pulsers, located on said integrated circuit and having outputs coupled to respective ones of said transducer elements, for selectively exciting said transducer elements to transmit a steered or focused ultrasonic wave; and a plurality of receivers, located on said integrated circuit and having inputs coupled to respective ones of said transducer elements, for receiving echo signals from said respective transducer elements.

46. In the ultrasonic diagnostic imaging system of claim 45, wherein said receivers comprise a plurality of amplifiers for amplifying echo signals received from said respective transducer elements.

47. In the ultrasonic diagnostic imaging system of claim 45, wherein said receivers further comprise means for coupling echo signals received from said respective transducer elements to channels of a receive beamformer.

48. In the ultrasonic diagnostic imaging system of claim 47, wherein said transducer pulsers have a plurality of inputs responsive to signals provided by a transmit beamformer for selectively exciting said transducer elements to transmit a steered or focused ultrasonic wave.

* * * * *